(12) United States Patent
Aldrich et al.

(10) Patent No.: US 7,038,078 B2
(45) Date of Patent: May 2, 2006

(54) METHODS OF SYNTHESIZING AND USING DERIVATIVES OF [2-(2-AMINOETHOXY) ETHOXY] ACETIC ACID

(75) Inventors: Jane V. Aldrich, Lawrence, KS (US); Vivek Kumar, Dublin, CA (US)

(73) Assignee: University of Marlyland, Baltimore, Baltimore, MD (US)

( * ) Notice: Subject to any disclaimer, the term of this patent is extended or adjusted under 35 U.S.C. 154(b) by 237 days.

(21) Appl. No.: 10/308,672

(22) Filed: Dec. 3, 2002

(65) Prior Publication Data

US 2003/0134989 A1 Jul. 17, 2003

Related U.S. Application Data

(63) Continuation-in-part of application No. PCT/US01/44382, filed on Nov. 26, 2001.
(60) Provisional application No. 60/253,242, filed on Nov. 27, 2000.

(51) Int. Cl.
*C07C 53/00* (2006.01)

(52) U.S. Cl. ................ 562/512; 562/523; 562/538; 562/540
(58) Field of Classification Search ............... 562/512, 562/523, 538, 540
See application file for complete search history.

(56) References Cited

FOREIGN PATENT DOCUMENTS

| EP | 194 972 | 9/1986 |
|----|---------|--------|
| EP | 410 280 | 1/1991 |
| EP | 618 222 | 10/1994 |
| WO | 01/36003 | 5/2001 |

OTHER PUBLICATIONS

Frisch et al, Bioconjugate Chem. 1996, vol. 7, pp 180–186.*
Renil, M.; Meldal, M., POEPOP and POEPS: Inert Polyethylene Glycol Crosslinked Polymeric Supports for Solid Synthesis, *Tet. Lett.*, 1996, 37, 6185–6188.
Renil, M.; Meldal, M., Synthesis and Application of a PEGA Polymeric Support for High–Capacity Continuous Flow Solid–Phase Peptide Synthesis, *Tet. Lett.*, 1995, 36, 4647–4650.
Adams, J. H.; Cook, R. M.; Hudson, D.; Jammalamadaka, V.; Lyttle, M. H.; Songster, M. F., A Reinvestigation of the Preparation, Properties, and Applications of Aminomethyl and 4–Methylbenzhydrylamine Polystyrene Resins, *J. Org. Chem.*, 1998, 63, 3706–3716.
Kates, S. A.; McGuiness, B. F.; Blackburn, C.; Griffin, G. W.; Sole, N. A.; Barany, G.; Albericio, F., "High–Load" Polyethylene Glycol–Polystyrene (PEG–PS) Graft Supports for Solid–Phase Synthesis, *Biopolymers (Peptide Science)*, 1998, 47, 365–380.
Anelli, P. L.; Biffi, C.; Montanari, F.; Quici, S., Fast and Selective Oxidation of Primary Alcohols to Aldehydes or to Carboxylic Acids and of Secondary Alcohols to Ketones Mediated by Oxammonium Salts under Two–Phase Conditions, *J. Org. Chem.*, 1987, 52, 2559–2562.
Atkinson, R. N.; Moore, L.; Tobin, J.; King, S. B.; Asymmetric Synthesis of Conformationally Restricted L–Arginine Analogues as Active Site Probes of Nitric Oxide Synthase, *J. Org. Chem.*, 1999, 64, 3467–3475.
Booth, R. J.; Hodges, J. C.; Solid–Supported Reagent Strategies for Rapid Purification of Combinatorial Synthesis Products, *Acc. Chem. Res.*, 1999, 32, 18–26.
Gavo, L. M., Solution–Phase Library Generation: Methods and Applications in Drug Discovery, *Biotechnol. and Bioeng.* (*Combinatorial Chemistry*), 1998, 61, 95–106.
Ferritto, R.; Seneci, P., High Throughput Purification Methods in Combinatorial Solution Phase Synthesis, *Drugs of the Future*, 1998, 23, 643–654.
Gooding, O. W.; Baudart S.; Deegan, T. L.; Heisler, K.; Labadie, J. W.; Newcomb, W. S.; Porco, Jr. J. A.; van Eikeren, P., On the Development of New Poly(styrene–oxyethylene) Graft Copolymer Resin Supports for Solid–Phase Organic Synthesis, *J. Comb. Chem.* 1999, 1, 113–122.
Snyder, K. R.; Story, S. C.; Heidt, M. E.; Murray, T. F.; DeLander, G. E.; Aldrich, J. v., Effect of Modification of the Basic Residues of Dynorphin A–(1–13) Amide on Kappa Opioid Receptor Selectivity and Opioid Activity, *J. Med. Chem.* 1992, 35, 4330–4333.
Delgado, C.; Francis, G. E.; Fischer, D.; The Uses and Properties of PEG–Linked Proteins, *Crit. In Rev. Ther. Drug Carrier Syst.*, 1992, 9, 249–304.
Zalipsky, S., Functionalized Poly(ethylene glycol) for Preparation of Biologically Relevant Conjugates, *Bioconjugate Chem.*, 1995, 6, 150–165.
Katre, N. V., The Conjugation of Proteins with Polyethylene glycol and Other Polymers, *Adv. Drug Delivery Rev.*, 1993, 10, 91–114.
Kramer, R. H.; Karpen, J. W., Spanning Binding Sites On Allosteric Proteins with Polymer–Linked Ligand Dimers, *Nature*, 1998, 395, 710–713.
Peters, R.; Sikorski, R., Ligand Binding. Molecular Barbells, *Science*, 1998, 282, 1439.
Terskikh, A. V.; Le Doussal, J.; Crameri, R.; Fisch, I.; Mach, J.; Kajava, A. V., "Peptabody": A New Type of High Avidity Binding Protein, *Proc. Natl. Acad. Sci. USA*, 1997, 94, 1663–1668.

(Continued)

*Primary Examiner*—Rita Desai
*Assistant Examiner*—Hector M. Reyes
(74) *Attorney, Agent, or Firm*—Pauley Petersen & Erickson

(57) ABSTRACT

A synthetic reaction to produce [2-(2-aminoethoxy)ethoxy] acetic acid (AEEA) derivatives. This synthetic reaction does not require isolation and purification of intermediates. The AEEA derivatives can be used to synthesize high load polystyrene-polyethylene glycol-like resins having excellent swelling characteristics.

36 Claims, 1 Drawing Sheet

OTHER PUBLICATIONS

Greenwald, R. B.; Pendri, A.; Conover, C. D.; Zhao, H.; Choe, Y. H.; Martinez, A.; Shum, K.; Guan, S., Drug Delivery Systems Employing 1,4– or 1,6–Elimination: Poly(ethylene glycol) Prodrugs of Amine–Containing Compounds, *J. Med. Chem.*, 1999, 42, 3657–3667.

Gruber, H. J.; Marek, M.; Schindler, H.; Kaiser, K., Biotin-Fluorophore Conjugates with Poly(ethylene glycol) Spacers Retain Intense Fluorescence After Binding to Avidin and Streptavidin, *Bioconjugate Chem.*, 1997, 8, 552–559.

Kaiser, K.; Marek, M.; Haselgrübler, T.; Schindler, H.; Gruber, H. J., Basic Studies on Heterobifunctional Biotin-PEG Conjugates with a 3–(4–Pyridyldithio)propionyl Marker on the Second Terminus, *Bioconjugate Chem.*, 1997, 8, 545–551.

Marek, M.; Kaiser, K.; Gruber, H. J., Biotin–Pyrene Conjugates with Poly(ethylene glycol) Spacers are Convenient Fluorescent Probes for Avidin and Streptavidin, *Bioconjugate Chem.*, 1997, 8, 560–566.

Kwok, K. Y.; McKenzie, D. L.; Evers, D. L.; Rice, K. G., Formulation of Highly Soluble Poly(ethylene glycol)–Peptide DNA Condensates, *J. Pharm. Sci.*, 1999, 88, 996–1003.

Wilbur, D. S.; Hamlin, D. K.; Pathare, P. M.; Weerawarna, S. A., Biotin Reagents for Antibody Pretargeting. Synthesis, Radioiodination, and in Vitro Evaluation of Water Soluble, Biotinidase Resistat Biotin Derivatives, *Bioconjugate Chem.*, 1997, 8, 572–584.

Boumrah, D.; Campbell, M. M.; Fenner, S.; Kinsman, R., Spacer Molecules in Peptide Sequences: Incorporation into Analogues of Atrial Natriuretic Factor, *Tetrahedron*, 1997, 53, 6977–6992.

Frisch, B.; Boeckler, C.; Schuber, F., Synthesis of Short Polyoxyethylene–Based Heterobifunctional Cross–Linking Reagents. Application to the Coupling of Peptides to Liposomes, *Bioconjugate Chem.*, 1996, 7, 180–186.

Atkinson, R. N.; Moore, L.; Tobin, J.; King, S. B., Asymmetric Synthesis of Conformationally Restricted L–Arginine Analogues as Active Site Probes of Nitric Oxide Synthase, *J. Org. Chem.*, 1999, 64, 3467–3475.

James Slama et al.: *The Synthesis of Glycolipids Containing a Hydrophilic Spacer–Group, Carbohydrate Research*, vol. 88, p. 213–221, Elsevier Scientific Publishing Co., Amsterdam, 1981.

Ari M.P. Koskinen et al.: *Synthesis of α–Helix Substituted Analogs of Calcitonin Gene–Related Peptide, Bioorganic & Medicinal Chemistry Letters*, vol. 5, No. 6, pp. 573–578, Elsevier Science Ltd., Great Britain, 1995.

* cited by examiner

METHODS OF SYNTHESIZING AND USING DERIVATIVES OF [2-(2-AMINOETHOXY) ETHOXY] ACETIC ACID

CROSS REFERENCE TO RELATED APPLICATION

This Patent Application is a Continuation-in-part Patent Application of PCTUS01/44382, filed 26 Nov. 2001, and claims the benefit of U.S. Provisional Application No. 60/253,242, filed 27 Nov. 2000.

STATEMENT REGARDING FEDERALLY SPONSORED RESEARCH

This invention was made with the support of the U.S. Government under Grant No. NIDA DA-10035 awarded by the National Institutes of Health. The U.S. Government has certain rights in this invention.

BACKGROUND OF THE INVENTION

1. Field of the Invention

The present invention is directed to a facile synthesis of polyethylene glycol (PEG)-like compounds of defined lengths (i.e., fixed monomer units). Specifically, a method is enumerated for the facile and cost-efficient synthesis of a suitably protected PEG-like spacer, for use under both solid-phase and solution-phase synthesis. More particularly, this invention is directed to a synthetic reaction to produce derivatives of [2-(2-aminoethoxy)ethoxy] acetic acid (AEEA), including the derivative allyloxycarbonyl-[2-(2-aminoethoxy)ethoxy] acetic acid (Alloc-AEEA). This invention is also directed to the use of AEEA derivatives to produce polystyrene-polyethylene-glycol-like (PPL) resins.

2. Description of Related Art

Polyethylene glycols are long chain organic polymers that are flexible, hydrophilic, enzymatically stable, and biologically inert. PEG chains, consisting of the common repeating ethylene glycol entity $[-CH_2-CH_2-O-]_n$, can be broadly divided into two types: 1) Polymeric PEG-based chains with molecular weights ranging from 1000 to >20,000 and 2) PEG-like chains of molecular weight <1000.

Polymeric PEG-based chains have been used in bioconjugates, and numerous reviews have described the attachment of this linker moiety to various molecules. The popularity of PEG-based technology is evident by the coining of the word "PEGnology," and by the ready and commercial availability of numerous PEG-based compounds.

As early as 1975, it was shown that PEG chains could help reduce the antigenicity and immunogenicity of proteins. This led to the attachment of PEG chains to various ligands and proteins for use in the fields of biochemistry and medicine. More recently, the hydrophilic character of PEG chains has been utilized in the design of prodrugs. PEG-based chains have also been used as spacers to enhance the fluorescent marker properties of fluorescent biotins. PEGylated DNA adducts have been used to study gene delivery. The amphiphilic nature of the PEG chains have also been utilized extensively to prepare hydrophilic polystyrene (PS)-PEG resins for use in solid-phase peptide synthesis (SPPS) as well as solid-phase organic synthesis (SPOS).

Although PEGylated molecules have numerous advantages as exemplified above, there are also disadvantages associated with these polymeric compounds. The main problem associated with PEG chains has been the lack of well-defined fixed molecular weight of the PEG chains. The variable chain lengths of high molecular weight PEGs (MW=1000 to 20,000 Da) not only impedes purification by size exclusion chromatography and characterization by mass spectrometry, but the problem multiplies if more than one PEG chain is attached per molecule. Thus, advances in analytical chemistry have made the use of polymeric PEG chains impractical in many instances. However, the properties of the PEG-based chains could be mimicked by shorter PEG-like spacers. PEG-like chains exhibit all of the properties of the polymeric PEG chains, but unlike the polymeric PEG chains, PEG-like spacers are made of defined lengths and molecular weights that can be easily controlled. Thus there is a growing technological need for improved PEG-like compounds as opposed to the traditional polymeric PEG chains.

Smaller PEG-like chains made up of between 2 to 6 ethylene glycol units have been used in many applications, especially in cases where the linker properties of the chains are more important than the polymer properties. The short PEG-like linkers can be classified into two types, the homo- $[X-(CH_2-CH_2-O)_n]-X$ and heterobifunctional $[X-(CH_2-CH_2-O)_n]-Y$ spacers. The heterobifunctional PEG-like spacers are becoming more popular mainly due to some recent reports of their synthesis (via multi-step synthetic routes) and applications of such compounds under both solution and solid-phase conditions.

PEG-like chains have primarily been used as spacers and linkers. For example, the homobifunctional PEG-like spacers have been used in the study of bivalent opioid ligands. Bivalent molecules of the type P-X-P, where P represents the pharmacophoric element (β-naltrexamine) and X the ethylene oxide spacer, have been synthesized and tested. It was found that differences in the spacer length (X) led to differences in selectivity of the bivalent ligands towards μ, κ and δ opioid receptors. In another example the commercially available homobifunctional linker, 4,7,10-trioxa-1,13-tridecanediamine was attached to biotin in order to increase its water solubility and to study the stability of this compound towards the enzyme biotindase.

Surprisingly, so far there have been only scant reports in the literature for the synthesis of heterobifunctional spacers. The synthesis of the unprotected diethylene glycol spacer $H_2N(CH_2CH_2O)_2CH_2COOH$ was reported in 1981, but the synthesis of the protected diethylene glycol spacer wasn't reported until 1995. The diethylene glycol spacer was synthesized independently by two groups and introduced into the peptide chain of calcitonin gene-related peptide (CGRP) and into analogs of atrial natriuretic factor (ANF).

The synthesis of a triethylene glycol spacer, Fmoc-NH(CH$_2$CH$_2$O)$_3$CH$_2$COOR was also reported in 1997 for incorporation into analogues of atrial natriuretic factor (ANF). The structure of Fmoc-AEEA is:

(1)

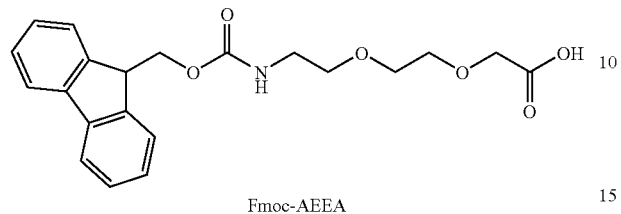

Fmoc-AEEA

Recently, the synthesis of the extended tetraethylene glycol spacer units Fmoc-NHCH$_2$CH$_2$COO(CH$_2$CH$_2$O)$_4$X (Fmoc-Ats where X=COCH$_2$CH$_2$COOH, Fmoc-Atg where X=CONHCH$_2$COOH, and Fmoc-Ata where X=CONHCH$_2$CH$_2$COOH) was reported and solid-phase Fmoc/t-Bu based strategy was used for incorporating these spacers into peptides. The interesting spacer BrCH$_2$CONH(CH$_2$CH$_2$O)$_3$CH$_2$COOH was designed and synthesized starting from tetraethylene glycol, and the diethylene glycol spacer maleyl-CH$_2$(CH$_2$OCH$_2$)$_2$COOH starting from H$_2$NCH$_2$(CH$_2$OCH$_2$)COOH. These compounds have been used to crosslink peptides to liposomes via solution chemistry in order to improve the immunogenic response of the small synthetic peptides for use in the development of vaccines for infectious diseases and cancer.

Although there has been a recent spurt in interest in these short chain PEG-like molecules, a low-cost commercial source of these compounds is still lacking. In particular, there is a need or desire for a solid-phase synthesis of labeled peptides (e.g. enkephalin derivatives) containing PEG-like spacers that not only decrease the hydrophobicity of the labeled peptides but also provide easy modulation of the spacer length to ensure accessibility of the labeled peptide to the receptor. Fluorenylmethoxycarbonyl-8-amino-3,6-dioxaoctanoic acid (Fmoc-NH(CH$_2$CH$_2$O)$_2$CH$_2$COOH) is available commercially, and provides the flexibility needed in terms of modulating both the hydrophobicity and spacer length. This spacer unit can be attached to peptides under solid-phase reaction conditions using a commercial reagent, but the high cost of the reagent (U.S.$466/g, Applied Biosystems, Foster City, Calif., U.S.A., and, U.S.$266/g Neosystem Groupe SNPE, Princeton, N.J., U.S.A.) limits the use of the commercial reagent under solid-phase conditions where excess reagent is typically used to drive reactions to completion.

Despite the cost, the prior art synthesis of [2-(2-aminoethoxy)ethoxy)] acetic acid (AEEA) involves four steps starting from commercially available 2-[2-(2-chloroethoxy)ethoxy]-ethanol 2 (Aldrich Chemical Co. Milwaukee, Wis., U.S.A.), as illustrated in Scheme 1. The chloride is first converted into an iodide by heating under reflux with sodium iodide in 2-butanone. The iodide is then converted into a phthalimido derivative 3 by treating it with potassium phthalimide. Oxidation of this compound with Jones reagent leads to the formation of carboxylic acid. Removal of the phthalimido group can be accomplished using hydrazine hydrate to obtain an amine hydrochloride 4. The overall yield after carrying out the four steps was found to be 23%. Although the conversion of the amine hydrochloride to the Fmoc-derivative 1 has not been reported, this compound should be readily available by reaction of AEEA with either Fmoc-Cl or Fmoc-OSu.

Scheme 1

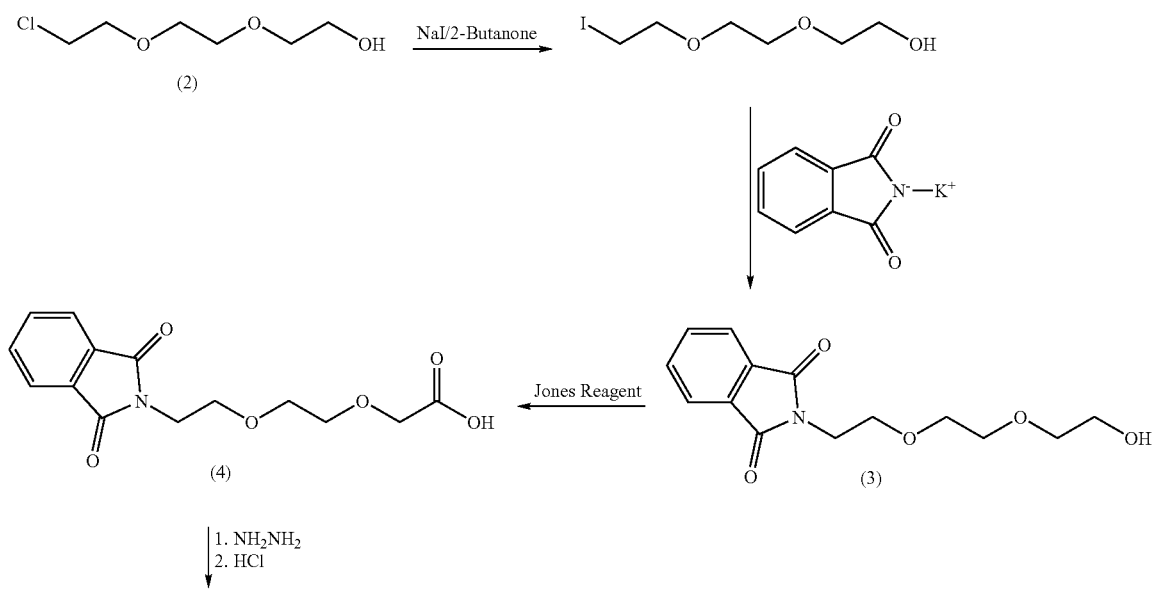

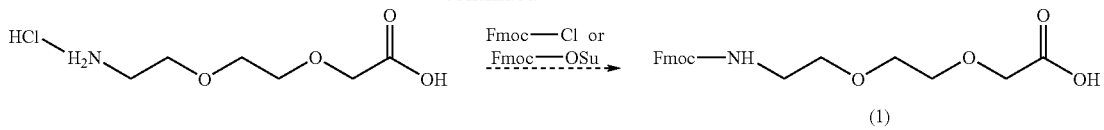

N-terminal analogs of calcitonin gene-related peptide (CGRP) have been synthesized where an AEEA unit was incorporated in the α-helical region of CGRP. The prior art synthesis of N-Fmoc-AEEA starting from 2-(2-aminoethoxy)ethanol is shown in Scheme 2. As shown, 2-(2-aminoethoxy)ethanol is dibenzylated followed by alkylation of the hydroxyl group with sodium hydride and methyl bromoacetate to obtain the methyl ester, which is then hydrolyzed to give the acid. Removal of the benzyl groups then gives AEEA as a white solid. The free amino acid is not isolated, but is converted directly into the Fmoc derivative using Fmoc-Cl. The overall yield of the final product after five steps is approximately 32%.

associated with peptide synthesis. However, the current focus for a majority of researchers in the field of solid-phase synthesis is the generation of small drug-like organic molecules, either to generate a new lead or to optimize a known active structure to improve pharmacological and/or pharmacokinetic properties (for example, solubility or in vivo permeability).

PS-PEG resins have been developed that are compatible with a wide array of transformations. PEG-based resins are either composed exclusively of PEG or of PEG supported on a polystyrene or polyamide backbone. Polystyrene has been modified by grafting PEG to the hydrophobic core of PS to produce a polymer that swells in both nonpolar and polar

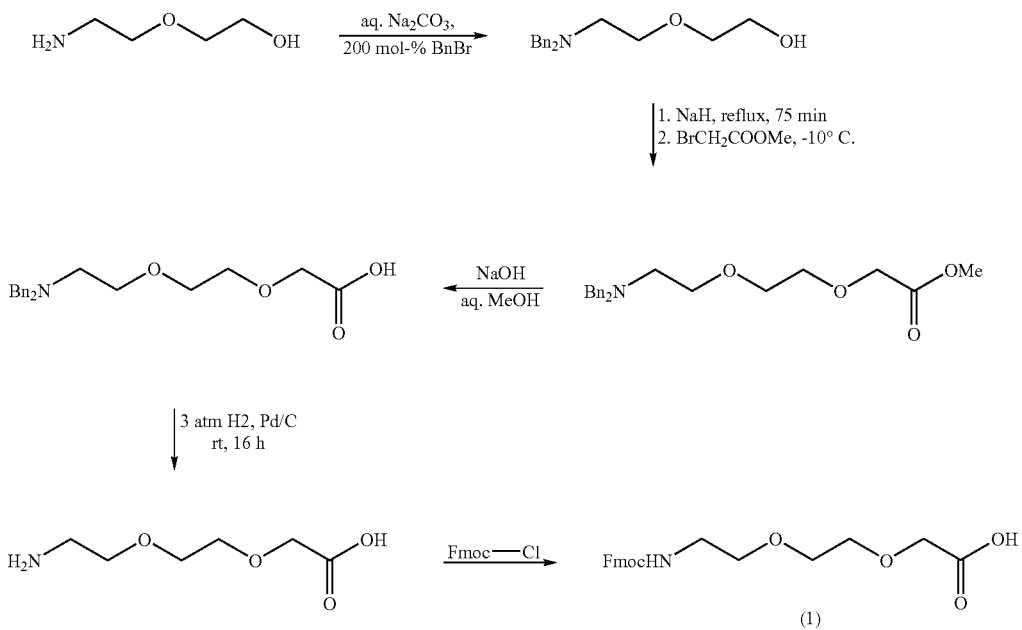

The two main drawbacks of the above two schemes are the low overall yields (23% and 32%, respectively) and the necessity for purification (by flash column chromatography, ion-exchange chromatography, etc.) of the intermediates at almost every step. Thus, neither of the two methods is well suited for a low-cost, multi-gram synthesis of the product.

As mentioned, PS-PEG resins are often used in solid-phase peptide synthesis (SPPS) as well as solid-phase organic synthesis (SPOS). Currently there is considerable interest in using solid-phase synthetic methods for the simultaneous preparation of large numbers and quantities of compounds. In the past, solid-phase synthesis was primarily solvents, and thus a broad range of solvents, including water, can be used during synthesis without drastic changes in bed volumes. Modern co-polymers consist of about 60–70% PEG with substitutions in the range of 0.1–0.4 mmol/g. PS-PEG resins exhibit improved physical and mechanical properties and can be used for both batchwise and continuous-flow solid phase synthesis. The excellent coupling and deblocking efficiencies during peptide synthesis on PS-PEG based resins have been attributed to the enhanced solvation of the derivatized PEG. These resins were therefore ideal candidates to be developed for SPOS, however the low initial loading of the reacting functional group (the free amine in the case of an amino resin) on these resins (typically 0.1–0.4 mmol/g) results in small quantities (typically ~50–100 mg/g of resin) of the molecules being synthesized.

More recently, solid-phase scavengers have been employed in parallel solution phase synthesis in order to purify compounds. Thus, automated parallel purification via nucleophilic and electrophilic scavenging of the resulting byproducts is possible in a cost-effective way using scavenger resins.

PS-PEG graft copolymer resins are prepared by one of two basic methods: (a) by anionic polymerization of ethylene oxide on to the resin to produce the graft resin in situ, e.g. TentaGel™, ArgoGel®, and NovaSyn® resins; or (b) by attachment of preformed PEGs (molecular weight up to ~3000 Da) to the resin, e.g. PEG-PS (Applied Biosystems) or Novagel® resins.

TentaGel™ resin (RAPP Polymere GmBh, Germany) has been widely used because of its mechanical stability and good swelling properties in organic and aqueous media. It is prepared by grafting ethylene oxide to hydroxymethyl polystyrene by anionic polymerization to give a support with 50–70% PEG content and average graft length of 68 ethyleneglycol units (3000 Da) with typical functional group loading in the range of 0.25–0.3 mmol/g. However, the acid lability of its benzylic ether linkage can be problematic.

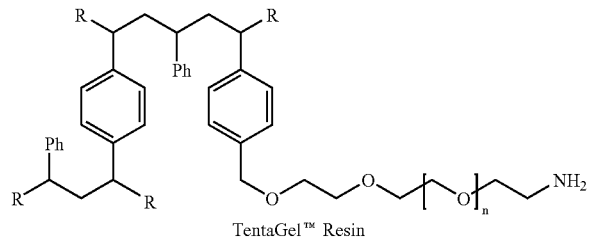
TentaGel™ Resin

ArgoGel® resin (Argonaut Technologies, San Carlos, Calif., U.S.A.) displays characteristics similar to the TentaGel™ resin. Bifurcation of the graft-polystyrene allows slightly higher loading and greater stability than analogous resins with a benzyl ether linkage. Its PEG content (about 67–82%) and average graft lengths (29–58 repeat units) were optimized to obtain functional group loading in the range of 0.4–0.5 mmol/g.

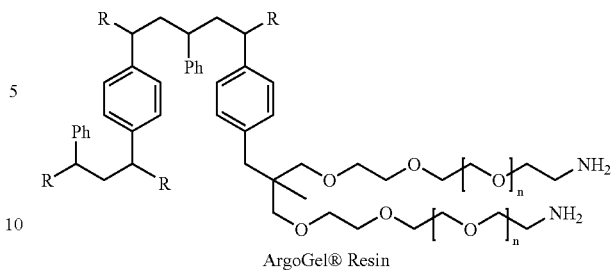
ArgoGel® Resin

The NovaSyn® TG resin (Novabiochem, San Diego, Calif., U.S.A.) overcomes the acid instability problem of TentaGel™ resin by polymerizing ethylene oxide on to a hydroxyethyl polystyrene resin. It is composed of low-cross-linked polystyrene grafted with PEG chains of molecular weight of 3000–4000 terminally functionalized with amino groups. Typical functional loading of the NovaSyn® resin is in the range of 0.2–0.5 mmol/g.

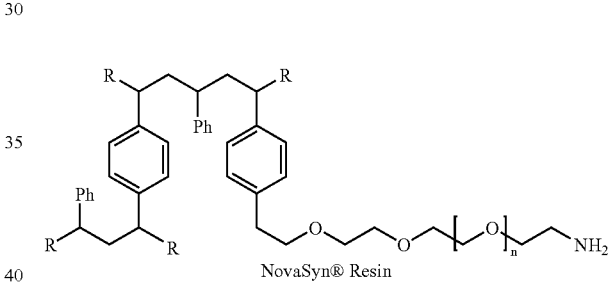
NovaSyn® Resin

While the PEG chain is polymerized onto the polystyrene core of TentaGel™, ArgoGel®, and NovaSyn® resins, an alternative form, marketed as PEG-PS resin by Applied Biosystems (Foster City, Calif., U.S.A.), has the preformed PEG chains attached to the polystyrene core via amide bonds. The low-load variety of the resin is prepared by coupling norleucine (as an internal reference amino acid) to functionalized 4-methylbenzhydrylamine (MBHA) polymer. Then a homobifunctional PEG-acid, prepared by reacting the diamino-PEG (molecular weight 2000) with succinic anhydride, is attached to the MBHA-Nle resin, providing the pendant carboxylic acid groups that are finally converted to amino groups (final loading 0.15–0.25 mmol/g) by reacting with ethylenediamine. A modest level of cross-linking also results.

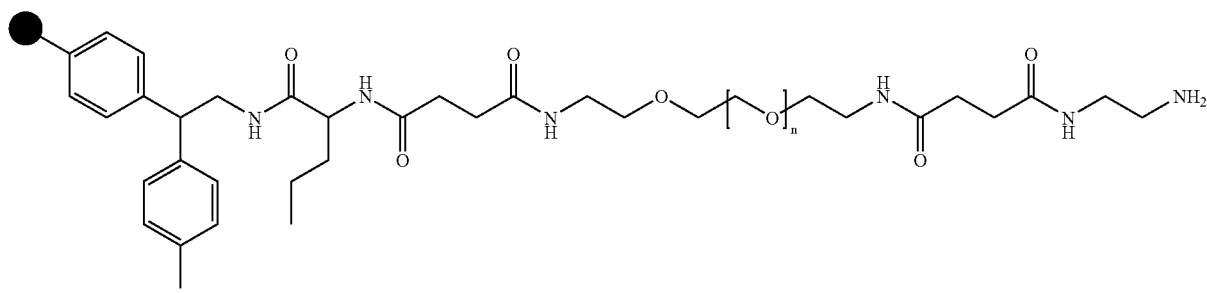

Low-Load Variety of PEG-PS Resin

A "high-load" (~0.25–0.45 mmol/g) variety of PEG-PS resin was prepared by following a similar strategy except that an ornithine residue [using Fmoc-Orn(Boc)-OH] was inserted instead of norleucine. The $N^\delta$-Boc was removed and a portion of the free amine (25–35%) was capped with acetic anhydride whereas the other half was available for subsequent synthesis. Final loading is typically around 0.6 mmol/g. A percent PEG content of between 40–70% was obtained in both the low-load variety and the high-load variety of PEG-PS, depending on the molecular weight of the diamino-PEG (PEG-600, PEG-900 and PEG-2001).

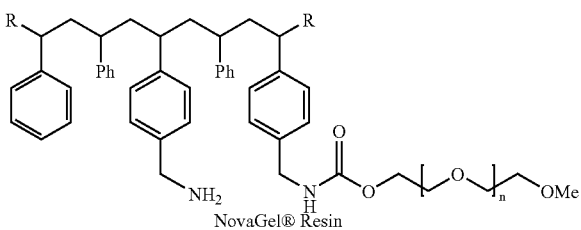

NovaGel® Resin

New solid-supports are constantly being developed in order to a) improve the chemical properties of the resin for

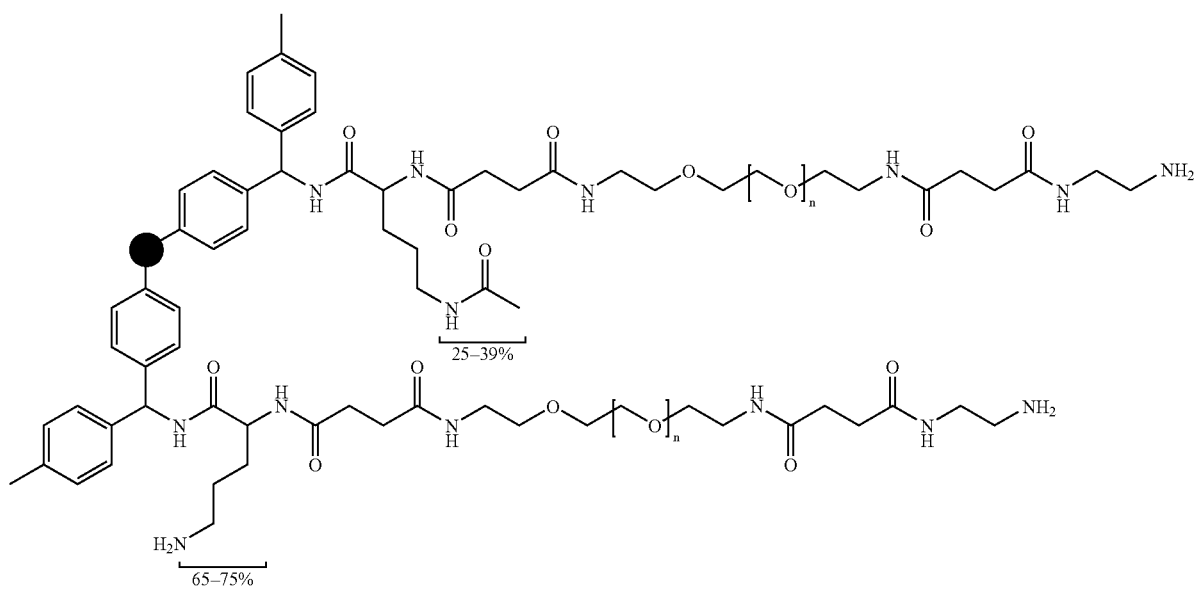

High-Load Variety of PEG-PS Resin

In the NovaGel® resin an aminomethylated resin is partially derivatized with methyl-$PEG_{2000}$-p-nitrophenylcarbonate. This produces a resin containing approximately 48% PEG, with a substitution of 0.7 mmol/g and good swelling characteristics. Also, the urethane linkage between the core resin and PEG is more stable to both piperidine and TFA (used for deprotection of Fmoc and Boc amine protecting groups, respectively), thus minimizing loss of the PEG chains during synthesis.

improved synthesis, b) optimize the physical properties of the beads for better performance and consistency, and/or c) to improve loading capacities of the beads to increase yields. One of the most important parameters that must be considered in designing solid supports is the swelling in various solvents. It is well known that resin beads must be well permeated by both solvents and reagents for the successful completion of any synthesis. Reactions will go to completion only if they are carried out in solvents that adequately swell the resins, and many poor synthetic results are probably due to poor swelling of the resin. For example, dichloromethane (DCM), which hydrogen bonds with the π electrons of the aromatic nuclei of polystyrene, is an excellent swelling solvent for this resin, and therefore syntheses carried out on PS resins in DCM will often go to completion with minimal impurities or side products.

The PEG portion of the PS-PEG resins influences both swelling in polar solvents as well as loading of the functional groups. PS-PEG resins exhibit excellent swelling over a wide range of solvents, from toluene (hydrophobic) to water (hydrophilic), a property that can contribute to a gain in synthetic efficiency. However, introduction of large PEG-based chains decreases resin loading so that loadings are typically much lower for PS-PEG resins (<0.2–0.4 mmol/g) than PS resins (>0.8–2.0 mmol/g). Also, the polymeric nature of the PEG chains can result in variable PEG content of the resin, which in turn affects loading. Thus, there is an interest in an easy and efficient method to obtain PS-PEG like resins with consistently high loading which could be efficiently utilized for both SPPS and SPOS conditions.

Although the PEG-PS based resins have been ideal for the synthesis of peptides, the low substitution level (0.1–0.7 mmol/g) is a problem. A high load resin with better swelling capacities in both hydrophilic and hydrophobic solvents would be very useful for these syntheses.

There is a need or desire for a synthetic reaction for producing AEEA derivatives that is economical and convenient.

There is a further need or desire for a synthetic reaction scheme for producing AEEA derivatives that does not require isolation and purification of intermediates.

There is yet a further need or desire for a synthetic reaction for producing high load resins having the physico-chemical properties of PS-PEG resins.

SUMMARY OF THE INVENTION

The present invention relates to a novel synthetic reaction scheme to produce [2-(2-aminoethoxy)ethoxy] acetic acid (AEEA) derivatives. This synthetic reaction scheme is economical and convenient because it does not require isolation and purification of intermediates. A novel AEEA derivative that can be produced is Alloc-AEEA (allyloxycarbonyl-[2-(2-aminoethoxy)ethoxy] acetic acid). Various other AEEA derivatives that can be produced include Fmoc-AEEA (fluorenylmethoxycarbonyl-[2-(2-aminoethoxy)ethoxy] acetic acid), Boc-AEEA (tert-butyloxycarbonyl-[2-(2-aminoethoxy)ethoxy] acetic acid), and Z-AEEA (benzyloxycarbonyl-[2-(2-aminoethoxy)ethoxy] acetic acid).

The AEEA derivatives can be used to synthesize high load polystyrene-polyethylene glycol-like (PPL) resins having excellent swelling characteristics. More particularly, the AEEA derivatives can be used to synthesize "designer resins" in which the properties of the resin can be easily optimized. This type of synthesis also permits the variation of the PEG-like content in order to optimize the physico-chemical characteristics versus the loading capacity. The resins can be readily synthesized using fluorenylmethoxy carbonyl-(aminoethoxy)ethyl acetic acid (Fmoc-AEEA) and an aminomethylated polystyrene (AMS) resin by standard solid-phase conditions.

The synthetic methods of the invention have potentially wide ranging applications in the fields of solid-phase peptide synthesis (SPPS) of small and large peptides and solid-phase organic synthesis (SPOS) of small organic molecules in drug design as lead compounds or for lead optimization.

DETAILED DESCRIPTION OF PREFERRED EMBODIMENTS

Figure 1:
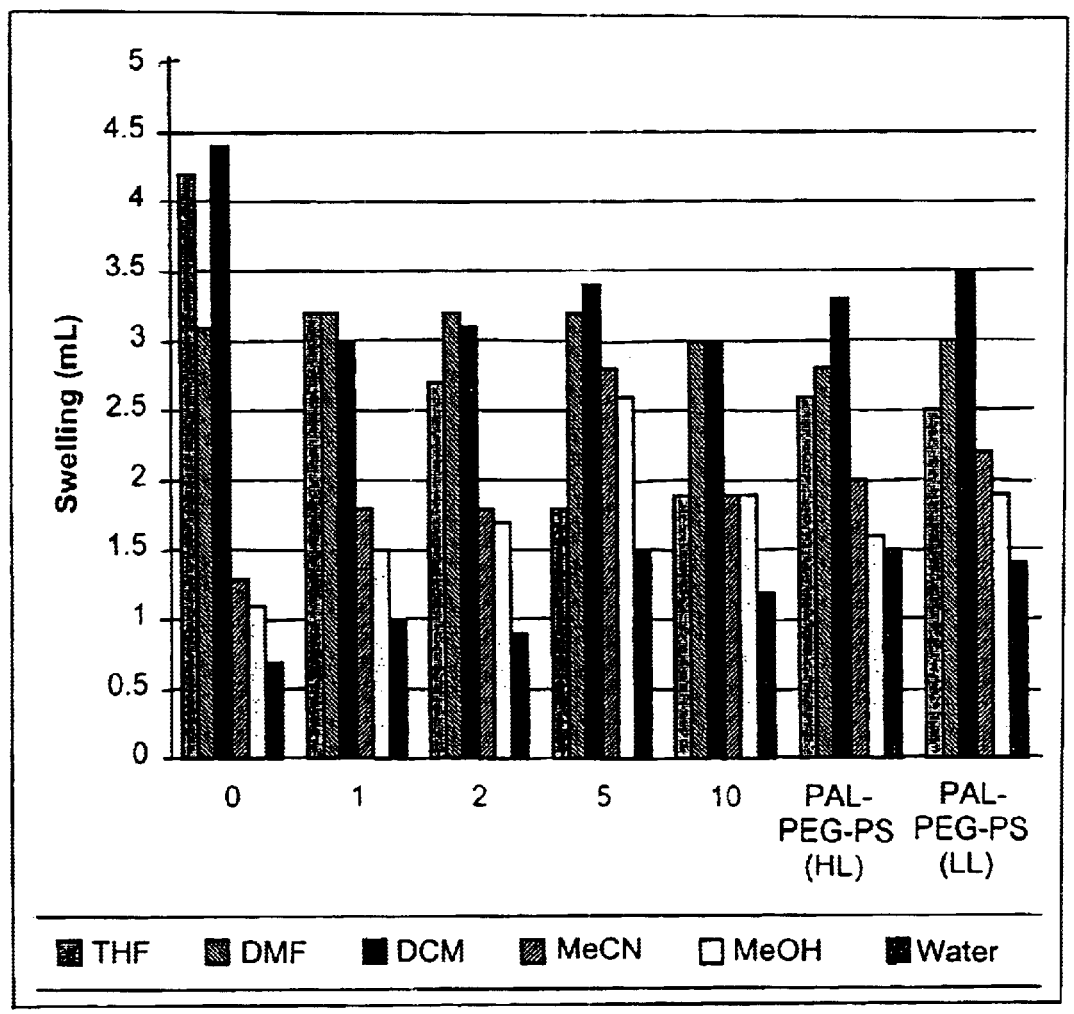
FIG. 1 is a chart showing swelling characteristics of various resins in various solvents, according to the data shown in Table 3.

The present invention is directed to an improved synthesis of [2-(2-aminoethoxy)ethoxy] acetic acid (AEEA) derivatives. A synthesis of [2-(2-aminoethoxy)ethoxy] acetic acid (AEEA) derivatives that differs from Scheme 1, above, can have a different order of reactions such that a phthalimido group is removed from an alcohol 3 rather than from an acid 4 and a resulting free amine can be purified using flash column chromatography. The free amino alcohol can then be converted to an Fmoc derivative, using Fmoc-Cl in 10% sodium carbonate, followed by Jones oxidation to give the final product 1, namely Fmoc-AEEA (fluorenylmethoxycarbonyl-[2-(2-aminoethoxy)ethoxy] acetic acid).

Unfortunately, after the usual workup and flash chromatography of the oily suspension, less than 5% Fmoc-AEEA may be obtained. PEG chains have been reported to be unstable under acidic conditions, and thus the low yield obtained could be a result of the extremely low pH (<1.0) involved in the Jones oxidation. TEMPO (2,2,6,6-tetramethyl-1-piperidinyloxy, free radical), a spin trapping reagent, in the presence of a catalytic amount of potassium bromide is known to catalyze the selective oxidation of primary and secondary alcohols to aldehydes and ketones by buffered hypochlorite. The addition of quaternary salts to the reaction mixture permits further oxidation of aldehydes to acids. TEMPO is not only selective but also relatively inexpensive (5 g/U.S.$58, Aldrich Chemical Co., Milwaukee, Wis., U.S.A.) and efficient with reactions going to completion within 5 minutes at 0° Celsius. The structure of TEMPO is illustrated as:

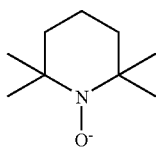

The product, Fmoc-AEEA, is easy to isolate and most importantly the entire synthesis can be carried out at 0° Celsius under mildly basic conditions (pH~8.5).

Thus, in the synthesis of the present invention, shown in Scheme 3 below, 2-[2-(2-chloroethoxy)ethoxy]-ethanol 2 is first converted to an azide using equimolar sodium azide in N,N-dimethylformamide (DMF) at 90–95° Celsius for 16 hours. The mixture is then diluted with anhydrous tetrahydrofuran (THF) and the salt byproduct removed by filtration. The solution is then subjected to Staudinger reaction conditions by reacting with 1.1 equivalents of triphenylphosphine, added in two equal portions within 15 minutes, for 24 hours followed by reaction with 1.1 equivalents of water for 24 hours. The solvents (THF and DMF) are evaporated on a rotary evaporator under reduced pressure and the free amine extracted with water (approximately 50 milliliters). The water-insoluble triphenylphosphine oxide and unreacted triphenylphosphine are removed by filtration. Sodium carbonate and Fmoc-Cl in THF are added to the aqueous extract and the reaction is then allowed to proceed overnight, or at least 8 hours, to obtain the Fmoc-derivative 5. The product is then oxidized using TEMPO and 5.25% NaOCl to give the final product 1 in 80% overall yield.

The same procedure outlined above can also be used to synthesize allyloxycarbonyl (Alloc), tert-butyloxycarbonyl (Boc), and benzyloxycarbonyl-(Z) derivatives of AEEA, having the following structure:

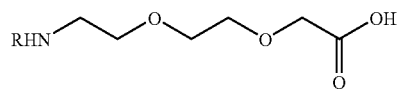

(6) R = Alloc
(7) R = Boc
(8) R = Z

AEEA Derivatives

One of these AEEA derivatives, allyloxycarbonyl (Alloc)-AEEA, having the structure shown above wherein R=Alloc, is believed to be a new compound.

As mentioned, the synthesis of the invention is an improvement over Scheme 1, described above, because the product is easy to isolate, the yield is much higher than the yield in Scheme 1, and the synthesis can be carried out at 0° Celsius under mildly basic conditions (pH~8.5).

The synthesis of the invention is also an improvement over Scheme 2, described above, because the synthesis of the present invention can be carried out in one pot and does not involve isolation of intermediates. Furthermore, in the present invention the amine is obtained as a free base via reduction of the azide under mild, safe and non-toxic

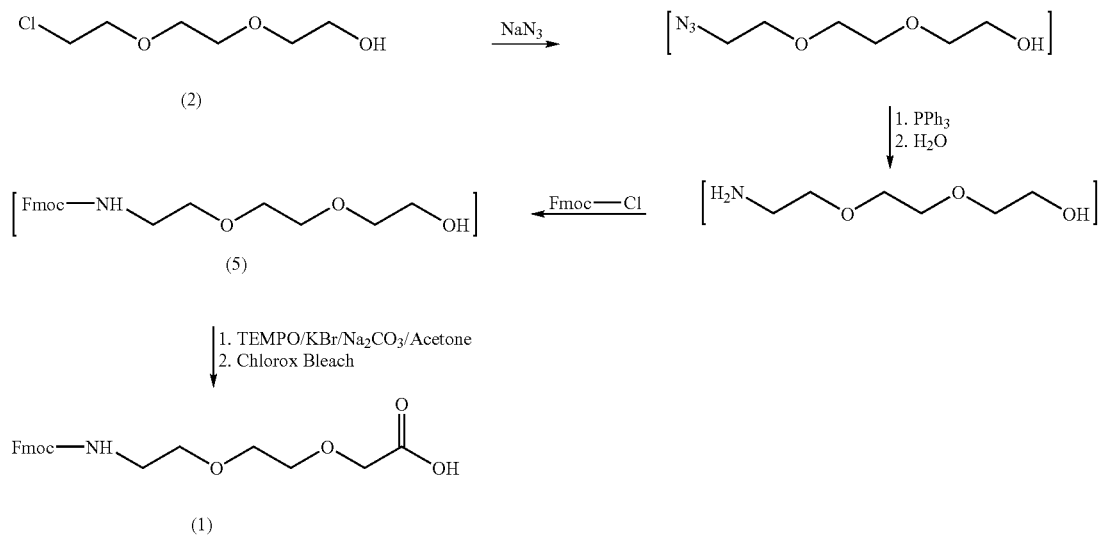

Scheme 3

The entire synthesis can be carried out on a multi-gram scale essentially as a "one-pot" synthesis without isolation of any of the intermediates. The final product is obtained as an oil after the acidification step, but crystallization commences almost immediately and the final product is obtained as crystalline colorless plates of >98% purity (by HPLC) from the aqueous mixture.

conditions, whereas in Scheme 2 the amine is obtained via the Gabriel synthesis, which is known to be highly variable at times, while the amine in the free base form is obtained via an ion-exchange column purification. The reaction conditions of the present invention are much milder than the reaction conditions of Scheme 2, with the present invention undergoing oxidation at 0° Celsius under mildly basic conditions (pH~8.5), and Scheme 2 undergoing oxidation at room temperature under highly acidic conditions (pH<1). In the present invention heavy metal reactants are avoided, whereas in Scheme 2 the oxidation step involves toxic chromic acid. The difference in cost in the synthesis of the compounds both in drug design and pharmacology, utilizing both solution-phase as well as solid-phase synthetic techniques. A summary of compounds that can be prepared according to the present invention, along with corresponding Chemical Abstracts Services (CAS) Registry Numbers, commercial sources, and costs, is provided in Table 1.

TABLE 1

Examples of AEEA Derivatives

| CA Index Name | Formula | CAS Number | Commercial Sources | U.S.$/g |
|---|---|---|---|---|
| Acetic Acid, [2-(2-aminoethoxy)ethoxy]- | $C_6H_{13}NO_4$ | 134978-97-5 | None | |
| 2,7,10-Trioxa-4-azadodecan-12-oic acid, 1-(9H-fluoren-9-yl)-3-oxa-(1) | $C_{21}H_{23}NO_6$ | 166108-71-0 | Applied Biosystems | 466 |
| 2,7,1 0-Trioxa-4-azadodecan-12-oic acid, 1-(9H-fluoren-9-yl)-3-oxa-(1) | $C_{21}H_{23}NO_6$ | 166108-71-0 | NeoSystem Groupe SNPE | 273 |
| Acetic Acid, [2-(2-Benzyloxycarbonyl-aminoethoxy)ethoxy]- (7) | $C_{14}H_{19}NO_6$ | 165454-06-8 | None | |
| Acetic Acid, [2-(2-tertbutyloxycarbonyl-aminoethoxy)ethoxy]- (6) | $C_{11}H_{21}NO_6$ | 161852-53-5 | Applied Biosystems | 300 |
| Acetic Acid, [2-(2-Allyloxyoxycarbonyl-aminoethoxy)ethoxyl]-(5) | $C_{10}H_{17}NO_6$ | None | None | | present invention and the synthesis of Scheme 2 is considerable, with the cost of the reagents of the present invention being minimal and further savings in not having to carry out purification steps compared to Scheme 2 in which the cost of the reagents is minimal but the multiple purification steps increases the cost of the synthesis at every step. In addition to the purification steps of Scheme 2 raising the cost of carrying out the synthesis, the multiple purification steps also limit the scale on which the synthesis can be performed and increase the level of difficulty of carrying out the synthesis compared to the lower level of difficulty of carrying out the present invention. Finally, the 80% overall yield of the present invention is considerably higher than the 23% overall yield of Scheme 2.

As shown in the Examples below, the overall yield varies among the different types of AEEA derivatives, with an overall yield of about 50% for Alloc-AEEA as an oil product to about 80% for Fmoc-AEEA as a solid. More particularly, the synthesis results in at least 50% overall yield as a solid or an oil product, or at least 65% overall yield as a solid or an oil product, or at least 80% overall yield as a solid or an oil product. Furthermore, the synthesis results in at least 35% overall yield as a salt product, or at least 50% overall yield as a salt product, or at least 70% overall yield as a salt product.

The present invention provides high yield and purity in the synthesis of 2-(2-aminoethoxy)ethoxy acetic acid (AEEA) derivatives. The high yield and purity obtained for the synthesis of these compounds coupled with their inherent hydrophilic nature enables a wide application of these Furthermore, it has been found that 8-aminoethoxyethyloxy acetic acid (AEEA), since it is a small PEG-like monomer possessing similar properties to the PEG-based molecules, can be used in place of longer polymeric PEG-based chains. Also, by a manipulation of the synthesis, multiple AEEA can be covalently linked together to achieve sizes similar to the larger polymeric PEG-based molecules. This linker unit can be incorporated onto a sufficiently high load aminomethyl polystyrene (AMS) resin to obtain high load PS-PEG like resin with properties comparable or better than currently available PS-PEG resins.

In particular, AEEA derivatives can be used to synthesize a first generation of PPL (Polystyrene-PEG-Like) designer resins. As described in the Examples below, PL-AMS was loaded with multiple (up to 10-mer) Fmoc-AEEA under automated Fmoc-chemistry using solid-phase methods. Analysis of the resin revealed that an optimum PEG content of approximately 40–50% is required for good swelling characteristics in various solvents. A combination of swelling studies and Fmoc quantitation revealed that loading the PL-AMS resin with a 5-mer of AEEA resulted in a resin with the best loading (0.54 mmol/g, 0.61 after Fmoc deprotection) and swelling characteristics. This resin was therefore picked for further development to obtain high load resins which retain excellent swelling characteristics. The ease of synthesis of these resins makes these truly designer resins with applications in the fields of SPPS and SPOS.

The present invention thus provides a cost-efficient facile synthesis for preparing AEEA derivatives in sufficient quantities for solid-phase synthesis which, in turn, can be used to prepare PPL designer resins. The invention has potential applications in such diverse fields as analytical chemistry, clinical biology, medicine, pharmacology, synthetic and surface chemistry and biosensors.

EXAMPLES

The following examples were carried out using the following materials from the following suppliers. 8-Chloro-3,6-dioxaoctan-1-ol, sodium azide, TEMPO, and potassium bromide were purchased from Aldrich Chemical Company (Milwaukee, Wis., U.S.A.). Dry solvents were purchased from Aldrich Chemical Company and used as such; all other solvents used were from EM Science (Gibbstown, N.J., U.S.A.). The solvent system used for HPLC was acetonitrile/water/trifluoroacetic acid (TFA) system. The HPLC column was a Vydac analytical column (C18, 300 A, 5 μ, 4.6×250 mm) equipped with a Vydac guard cartridge. Samples were eluted using a linear gradient of 10–85% solvent B over 50 minutes with a flow rate of 1.5 mL/min and detected at 214 nm; solvent A was aqueous 0.1% TFA and solvent B was MeCN containing 0.1% TFA. The samples were analyzed by fast atom bombardment mass spectrometry (FAB-MS) using a Kratos MS 50 RFTC instrument in the positive mode in the Environmental Health Sciences Center at Oregon State University, Corvallis, Oreg. and by electrospray ionization mass spectrometry (ESI-MS) using a Finnigan MAT LCQ mass spectrometer in the positive mode at the Department of Pharmaceutical Sciences, University of Maryland, Baltimore, Md., U.S.A. Synthesis of 8-Fluorenylmethoxycarbonylamino-3,6-dioxaoctanoic acid. (1)

A 100-mL round-bottom flask was charged with 8-chloro-3,6-dioxaoctan-1-ol (3.25 g, 19.4 mmol), sodium azide (1.25 g, 19.4 mmol), and 25 mL dry N,N-dimethylformamide (DMF) under nitrogen, stoppered and stirred overnight at 90° Celsius, and then cooled and diluted with 100 mL of dry tetrahydrofuran (THF). The precipitated salts were removed by rapid filtration and 1.1 equivalents of triphenylphosphine (5.6 gm, 20.9 mmol) were added in two batches (2.8 g each) over 15 minutes. Nitrogen evolution began almost immediately. A DriRite® guard-tube was placed over the flask and the mixture stirred for 24 hours at which time 1.5 equivalents of water (0.6 mL) was added to the mixture. The solution was stirred for an additional 24 hours; the solvents were evaporated under reduced pressure, first at 45° Celsius to remove THF and then at 55–60° Celsius to remove DMF, to obtain an oily solid. To this was added 40 mL water and the precipitated solids removed by filtration. The solids were washed with 3×5 mL water and then discarded. The filtrate and washings were combined, anhydrous sodium carbonate (5.5 gm) was added to the aqueous solution, and the solution cooled to <5° Celsius. Fmoc-Cl (5.0 g, 19.4 mmol) dissolved in 25 mL THF was added dropwise to the cold solution over 30 minutes. The mixture was stirred at 5° Celsius for 1 hour and then at room temperature overnight. TLC (EtOAc) indicated the absence of starting material ($R_f$<0.1, ninhydrin positive) and formation of the Fmoc-protected alcohol ($R_f$= 0.3). The THF was evaporated at 45° Celsius under reduced pressure and the aqueous layer extracted with EtOAc (6×50 mL); the EtOAc extract was then dried over $MgSO_4$ and evaporated to obtain the product as a yellow oil (7.4 g): FAB-MS m/z 372 $(M+H)^+$.

Acetone (95 mL) was added to this oil and the solution cooled to −10 to −5° Celsius in an ethylene glycol/dry ice slush bath. To the cold solution was added a mixture of aqueous 5% sodium bicarbonate (95 mL), KBr (0.225 g, 1.9 mmol) and TEMPO (3.4 gm, 22 mmol, as a suspension) such that the temperature was maintained below 0° Celsius. To this mixture an aqueous NaOCl solution (30.0 mL, 25.6 mmol, 5.25% Chlorox® bleach) was added dropwise over 10 minutes. After 1 hour at 0° Celsius, additional aqueous NaOCl (14.3 mL, 12.2 mmol) was added over 5 minutes. The temperature was maintained at 0° Celsius for an additional hour, at which time the cold bath was removed and the reaction mixture stirred overnight at room temperature. The acetone was evaporated at 45° Celsius under reduced pressure, and the yellow-orange solution extracted (in a fume-hood) with EtOAc (6×50 mL) until the aqueous layer turned colorless. Ice-chips (50 g) were added to the colorless solution and the solution acidified (to pH~2) using 1 N HCl (approximately 50–55 mL). The oily semisolid started to crystallize almost immediately, and was refrigerated overnight at 4° Celsius. The crystals obtained were filtered and dried in vacuo to give the final product as shiny white plates (6.0 g, 80% overall yield). Since the Fmoc derivative was a solid, it was not converted to a salt, so its overall yield was 80%. The purity of the final product as determined by HPLC (>98%) deemed recrystallization unnecessary: melting point=95–97° Celsius; TLC: $R_f$(EtOAc/MeOH/AcOH, 9/1/0.025) 0.3, HPLC: $t_R$ 35 minutes (>99% purity) (both TLC and HPLC samples coeluted with authentic commercial sample); FAB-MS m/z 386 $(M+H)^+$(Calc. 385.0). $^1$H NMR ($CDCl_3$) δ 7.77–7.29 (m, 8H), 5.25 (bs, 1H), 4.41–4.39 (d, 2H), 4.24–4.20 (t, 1H), 4.16 (s, 2H), 3.75–3.39(m, 8H).

Synthesis of 8-Allyloxycarbonylamino-3,6-dioxaoctanoic acid (6)

This compound was prepared in 50% yield as a yellow oil from 8-chloro-3,6-dioxaoctan-1-ol (3.35 g, 20.0 mmol) using allyloxy chloroformate (2.4 g, 20 mmol) in place of Fmoc-Cl as described above. $^1$H NMR ($CDCl_3$) δ 6.15–5.85 (m, 1H), 5.26–5.45 (m, 2H), 4.5 (s, 2H), 4.2 (s, 2H), 3.35–3.85 (m, 8H). ESI-MS 248.0 $(M+H^+)$ (Calcd: 247.2).

To a solution of 0.50 g of the above compound in ether (20 mL) was added dicyclohexylamine (0.34 mL) and the mixture was stirred overnight. Petroleum ether (35–60° Celsius) was added slowly to the clear solution until a slight turbidity was observed. Refrigeration over a 2-day period yielded crystals, which were filtered and dried to give the dicyclohexylamine salt (0.65 g, 75% yield): mp 74–77° Celsius. Anal. ($C_{10}H_{17}NO_6$) Calcd. C, 61.66; H, 9.41; N, 6.54; O. Found C, 61.50; H, 9.43; N, 6.47. The overall yield for the salt was the yield of the reaction sequence (50%) times the yield for the formation of the salt (75%), which in this case was 37.5%.

Synthesis of 8-tert-butyloxycarbonylamino-3,6-dioxaoctanoic acid (7)

This compound was prepared in 83% overall yield (4.3 g) as a thick yellow oil from 8-chloro-3,6-dioxaoctan-1-ol (3.35 g, 20.0 mmol) using Boc-carbonate (4.36 g, 20 mmol) in place of Fmoc-Cl in the procedure described above. $^1$H NMR (CDCl$_3$) δ 4.18 (s, 2H), 4.2 (s, 2H), 3.34–3.77 (m, 8H), 1.5 (s, 9H). ESI-MS 264.1 (M+H$^+$) (Calcd. 263.1).

To a solution of the above compound (0.50 g) in ether (20 mL) was added dicyclohexylamine (0.34 mL) and the mixture stirred overnight. The amorphous powder was filtered, washed with ether (25 mL) and dried to give the dicyclohexylamine salt (0.74 g, 88%): mp 113–115° Celsius. The overall yield for the salt was the yield of the reaction sequence (83%) times the yield for the formation of the salt (88%), which in this case was 73%.

Synthesis of 8-Benzyloxycarbonylamino-3,6-dioxaoctanoic acid (8)

This compound was prepared in 83% overall yield (4.9 g) as a thick yellow oil from 8-chloro-3,6-dioxaoctan-1-ol (3.35 g, 20.0 mmol) using benzylchloroformate (3.4 g, 20 mmol) in place of Fmoc-Cl in the procedure as described above. $^1$H NMR (CDCl$_3$) δ 7.35 (s, 5H), 5.28 (bs, 1H), 5.10 (s, 2H), 4.15 (s, 2H), 3.41–3.74 (m, 8H). ESI-MS 297.9 (M+H$^+$) (Calcd: 297.1).

To a solution of the above compound (0.50 g) in ether (20 mL) was added dicyclohexylamine (0.31 mL) and the mixture was stirred overnight. The amorphous powder filtered, washed with ether (25 mL) and dried to give the dicyclohexylamine salt (0.69 g, 85%): mp 84–86° Celsius. The overall yield for the salt was the yield of the reaction sequence (83%) times the yield for the formation of the salt (85%), which in this case was 70.5%.

Synthesis of PPL Designer Resins

Fmoc-AEEA was attached to a high load PL-AMS (Polymer Laboratories, Amherst, Mass.) resin (1.41 mmol/g initial loading, as determined by quantitative ninhydrin analysis). Resins were prepared containing PEG-like chains of different lengths (1-, 2-, 5- and 10-mers). The linker length was varied to determine the optimum % PEG-like content needed to maintain appropriate swelling in polar solvents while maintaining high loading.

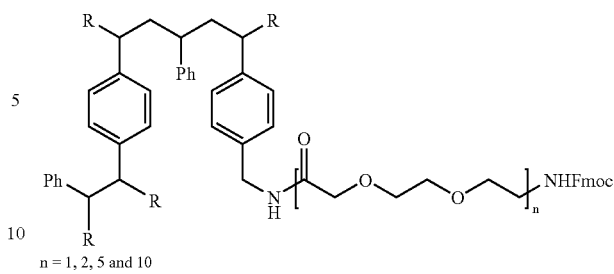

n = 1, 2, 5 and 10

Stepwise solid-phase synthesis was carried out on a Biosearch 9500 automated peptide synthesizer using standard Fmoc strategy. Fmoc-AEEA (3 equiv) was coupled to PL-AMS resin [1.41 mmol/g (1.75 mmol/g reported)] in N,N-dimethylacetamide (DMA) under solid-phase conditions in 2 hours. N,N-Diisopropylcarbodiimide (DIC) and 1-hydroxybenzotriazole (HOBt) were used for all couplings. The completeness of the coupling reactions was monitored by the qualitative ninhydrin test. The Fmoc group was then removed using 20% piperidine in DMA over 10 minutes and the coupling/deprotection steps repeated until a resin with the desired length of the PEG-like chain was obtained. After coupling the last monomer, the resin was washed with DMA, DCM and MeOR (3×2 min each) and dried overnight in vacuo. Multiple linker units were successfully incorporated without the need for double coupling reactions or the need for other forcing conditions in order to drive the reactions to completion.

The Fmoc group was then determined quantitatively according to a slight modification of a reported procedure. Approximately 5 mg of accurately weighed resin were mixed with piperidine (4 mL) and DCM (4 mL) in a 25 mL volumetric flask. After 30 min with occasional stirring, 1.6 mL MeOH were added to quench the reaction. The volume was adjusted to 25 mL using DCM. Aliquots were filtered (using glass-wool inserted into a Pasteur pipette) directly into the cuvette and the absorbance read at 301 nm. The loading was then calculated according to the following formula:

$$\text{Loading (mmol/g)} = [A]_{301} \times 25 \text{ mL}/7800 \text{ M}^{-1}\text{cm}^{-1} \times 1 \text{ cm} \times [g]$$

Four readings per sample were recorded and the loading was calculated as the average of two samples; the results are presented in Table 2.

TABLE 2

Percent PEG Content and Loading

| L$_n$-AMS (n) | MW of Fmoc-(AEEA) | % AEEA | Expected Loading (mmol/g) | Observed Loading (mmol/g) | Calculated Unprotected* Loading (mmol/g) |
|---|---|---|---|---|---|
| 0 | — | 0 | 1.75 | 1.41 | 1.41 |
| 1 | 385 | 12 | 0.91 | 0.84 (92%) | 1.03 |
| 2 | 530 | 21 | 0.81 | 0.73 (90%) | 0.87 |
| 5 | 965 | 39 | 0.60 | 0.54 (90%) | 0.61 |
| 10 | 1676 | 48 | 0.39 | 0.33 (85%) | 0.36 |
| Fmoc-PAL-PEG-PS (HL) | — | | 0.43 | — | 0.54 |
| Fmoc-PAL-PEG-PS (LL) | | | 0.16 | — | 0.17 |

*After Fmoc removal

Swelling studies (see Table 3, FIG. 1) were performed on 0.5 g of resin (approximate dry volume 0.75 mL) in a 10 mL graduated cylinder using 5 mL of the solvent. The resin was vortexed for 30 seconds at 30-minute intervals and the swelling recorded after 1 hour. The resin was then washed sequentially with DCM and MeOH (3×2 minutes) and dried overnight before the next study. When the solvent was water, the resin was washed with DMF, DCM and MeOH (3×2 minutes) and dried overnight.

TABLE 3

Swelling Studies

| L$_n$-AMS (n) | Swelling (mL) | | | | | |
|---|---|---|---|---|---|---|
| | DCM | DMF | THF | MeOH | MeCN | Water |
| 1 | 3.0 | 3.2 | 3.2 | 1.5 | 1.8 | 1.0 |
| 2 | 3.1 | 3.2 | 2.7 | 1.7 | 1.8 | 0.9 |
| 5 | 3.4 | 3.2 | 1.8 | 2.6 | 2.8 | 1.5 |
| 10 | 3.0 | 3.0 | 1.9 | 1.9 | 1.9 | 1.2 |
| 0 (AMS) | 4.4 | 3.1 | 4.2 | 1.1 | 1.3 | 0.7 |
| Fmoc-PAL-PEG-PS (LL) | 3.5 | 3.0 | 2.5 | 1.9 | 2.2 | 1.4 |
| Fmoc-PAL-PEG-PS (HL) | 3.3 | 2.8 | 2.6 | 1.6 | 2.0 | 1.5 |

(L) = 2-[2(2-Aminoethoxy)ethoxy]acetyl-

FIG. 1 is a graphical representation of the data shown in Table 3. Initial experiments revealed that the PEG-like linker could be attached to the PL-AMS resin without the need for double coupling or extension of the coupling times; up to 10 linker units were attached without difficulty. Approximately 40% PEG (with a loading of 0.54 mmol/g) was obtained with 5 AEEA units loaded onto the 1.41 mmol/g PL-AMS resin, and 48% PEG (with a loading of 0.33 mmol/g) was obtained with 10 units. Excellent swelling in polar solvents was observed in both cases (Table 3), and therefore it was decided to not increase linker length further at this point, since the additional weight gain would only reduce the loading. These swelling studies revealed that optimum PEG content (40–50%) necessary for good swelling in polar solvents was less than thought previously (60–80%). The % PEG content and loading can be further optimized by synthesizing the 3- and 4-mer resins. Similar results were obtained using a lower initial load (0.91 mmol/g) PL-AMS resin, although as expected the functional group loading was considerably lower. Comparison of the swelling characteristics of the high-load (HL) and low-load (LL) PEG-PS resins with the synthesized resins (FIG. 1) showed that the 5-mer resin not only had a higher loading but also had equal or better swelling in all solvents except THF.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A method of synthesizing a [2-(2-aminoethoxy)ethoxy)] acetic acid derivative, comprising the steps of:

converting 2-[2-(2-chloroethoxy)ethoxy]-ethanol to an azide derivative using equimolar sodium azide in N,N-dimethylformamide;

diluting the azide derivative with anhydrous tetrahydrofuran;

removing a salt byproduct from the azide derivative by filtration;

reacting the azide derivative with triphenylphosphine, followed by reaction with water;

evaporating the N,N-dimethylformamide and the anhydrous tetrahydrofuran;

dissolving a free amine from the azide derivative in water, creating an amine solution;

removing water-insoluble triphenylphosphine oxide and unreacted triphenylphosphine from the amine solution, leaving an aqueous extract;

adding sodium carbonate and R—Cl in tetrahydrofuran to the aqueous extract and allowing the reaction to proceed to obtain an R-derivative, wherein R is selected from the group consisting of allyloxycarbonyl, fluorenylmethoxycarbonyl, tert-butyloxycarbonyl, and benzyloxycarbonyl; and oxidizing the R-derivative with 2,2,6,6-tetramethyl-1-piperidinyloxy to give the [2-(2-aminoethoxy)ethoxy)] acetic acid derivative.

2. The method of claim 1, wherein the [2-(2-aminoethoxy)ethoxy)] acetic acid derivative comprises allyloxycarbonyl-[2-(2-aminoethoxy)ethoxy] acetic acid, fluorenylmethoxycarbonyl-[2-(2-aminoethoxy)ethoxy] acetic acid, tert-butyloxycarbonyl-[2-(2-aminoethoxy)ethoxy] acetic acid, or benzyloxycarbonyl-[2-(2-aminoethoxy)ethoxy] acetic acid.

3. The method of claim 1, wherein allyl chloroformate is used in place of R—Cl to obtain allyloxycarbonyl-[2-(2-aminoethoxy)ethoxy] acetic acid.

4. The method of claim 1, wherein the N,N-dimethylformamide and the anhydrous tetrahydrofuran are evaporated on a rotary evaporator under reduced pressure.

5. The method of claim 1, wherein the water-insoluble triphenylphosphine oxide and the unreacted triphenyiphosphine are removed from the amine solution by filtration, leaving the aqueous extract.

6. The method of claim 1, wherein 2,2,6,6-tetramethyl-1-piperidinyloxy and 5.25% NaOCl are used to oxidize the R-derivative to give the [2-(2-aminoethoxy)ethoxy)] acetic acid derivative.

7. The method of claim 1, wherein the synthesis of the [2-(2-aminoethoxy)ethoxy)] acetic acid derivative results in at least 50% overall yield as a solid or oil product.

8. The method of claim 1, wherein the synthesis of the [2-(2-aminoethoxy)ethoxy)] acetic acid derivative results in at least 65% overall yield as a solid or oil product.

9. The method of claim 1, wherein the synthesis of the [2-(2-aminoethoxy)ethoxy)] acetic acid derivative results in at least 80% overall yield as a solid or oil product.

10. The method of claim 1, wherein the synthesis of the [2-(2-aminoethoxy)ethoxy)] acetic acid derivative results in at least 35% overall yield as a salt product.

11. The method of claim 1, wherein the synthesis of the [2-(2-aminoethoxy)ethoxy)] acetic acid derivative results in at least 50% overall yield as a salt product.

12. The method of claim 1, wherein the synthesis of the [2-(2-aminoethoxy)ethoxy)] acetic acid derivative results in at least 70% overall yield as a salt product.

13. The method of claim 1, wherein the [2-(2-aminoethoxy)ethoxy)] acetic acid derivative comprises fluorenylmethoxycarbonyl-[2-(2-aminoethoxy)ethoxy] acetic acid, tert-butyloxycarbonyl-[2-(2-aminoethoxy)ethoxy] acetic acid, or benzyloxycarbonyl-[2-(2-aminoethoxy)ethoxy] acetic acid.

14. A method of synthesizing a [2-(2-aminoethoxy)ethoxy] acetic acid derivative, comprising the steps of:
(a) converting 2-[2-(2-chloroethoxy)ethoxyl]-ethanol to an azide derivative;
(b) reducing the azide derivative to its corresponding amine;
(c) reacting the amine to obtain an R-derivative, wherein R is a suitable protecting group; and
(d) oxidizing the R-derivative to give the [2-(2-aminoethoxy)ethoxy)] acetic acid derivative.

15. The method of claim 14, wherein R is allyloxycarbonyl, fluorenylmethoxycarbonyl, tert-butyloxycarbonyl or benzyloxycarbonyl.

16. The method of claim 14, wherein the converting step (a) is carried out in N,N-dimethylformamide.

17. The method of claim 14, wherein the converting step (a) is carried out with sodium azide.

18. The method of claim 14, wherein the converting step (a) is carried out using equimolar sodium azide in N,N-dimethylformamide.

19. The method of claim 14, wherein the converting step (a) comprises diluting the azide derivative with anhydrous tetrahydrofuran.

20. The method of claim 14, wherein the converting step (a) is carried out using sodium azide in N,N-dimethylformamide, and wherein the converting step (a) comprises diluting the azide derivative with anhydrous tetrahydrofuran.

21. The method of claim 20, further comprising evaporating the N,N-dimethylformamide and the anhydrous tetrahydrofuran after the reducing step (b).

22. The method of claim 14, wherein the converting step (a) comprises removing any salt byproduct from the azide derivative.

23. The method of claim 14, wherein the reducing step (b) comprises reacting the azide derivative with triphenyiphosphine, followed by reacting with water, so as to yield the corresponding amine.

24. The method of claim 23, further comprising dissolving the corresponding amine of reducing step (b) in water and removing any water-insoluble triphenyiphosphine oxide or unreacted triphenyiphosphine, yielding an aqueous solution of the corresponding amine.

25. The method of claim 24, wherein the reacting step (c) comprises adding sodium carbonate and R—Cl to the aqueous solution of the corresponding amine.

26. The method of claim 24, wherein the reacting step (c) comprises adding sodium carbonate and R—Cl in tetrahydrofuran to the aqueous solution of the corresponding amine.

27. The method of claim 24, wherein the reacting step (c) comprises adding sodium carbonate and di-tert-butyl dicarbonate to the aqueous solution of the corresponding amine.

28. The method of claim 14, wherein the reacting step (c) is carried out using sodium carbonate and R—Cl.

29. The method of claim 14, wherein the reacting step (c) is carried out using sodium carbonate and R—Cl in tetrahydrofuran.

30. The method of claim 14, wherein the reacting step (c) is carried out with allyl chloroformate.

31. The method of claim 14, wherein the oxidizing step (d) comprises using 2,2,6,6-tetramethyl-1-piperidinyloxy.

32. The method of claim 14, wherein the oxidizing step (d) comprises using aqueous NaOCl.

33. The method of claim 14, wherein the oxidizing step (d) comprises using 2,2,6,6-tetramethyl-1-piperidinyloxy and aqueous NaOCl.

34. The method of claim 14, wherein the oxidizing step (d) is carried out using 2,2,6,6-tetramethyl-1-piperidinyloxy, KBr, Na₂CO₃, acetone and bleach.
35. The method of claim 14, the method being further characterized by the absence of any isolation and purification of any intermediates.
36. A compound of the general formula
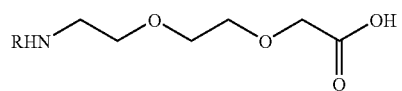
wherein R comprises allyloxycarbonyl.
* * * * *

UNITED STATES PATENT AND TRADEMARK OFFICE
CERTIFICATE OF CORRECTION

| | | |
|---|---|---|
| PATENT NO. | : 7,038,078 B2 | Page 1 of 1 |
| APPLICATION NO. | : 10/308672 | |
| DATED | : May 2, 2006 | |
| INVENTOR(S) | : Jane V. Aldrich et al. | |

It is certified that error appears in the above-identified patent and that said Letters Patent is hereby corrected as shown below:

Column 16 line 20,
In Table 1, delete CAS Number 161852-53-5 for "Acetic Acid, [2-(2-tertbutyloxycarbonyl-aminoethoxy)ethoxy]- (6)" and in its place insert CAS Number 108466-89-3.

Signed and Sealed this

Twenty-fifth Day of July, 2006

JON W. DUDAS
*Director of the United States Patent and Trademark Office*